United States Patent [19]

Giordano et al.

[11] Patent Number: 5,274,186
[45] Date of Patent: * Dec. 28, 1993

[54] INTERMEDIATES AND THEIR USE IN THE SYNTHESIS OF ORGANIC COMPOUNDS

[75] Inventors: Claudio Giordano, Monza; Graziano Castaldi, Briona, both of Italy

[73] Assignee: Zambon S.p.A., Italy

[*] Notice: The portion of the term of this patent subsequent to Apr. 2, 2008 has been disclaimed.

[21] Appl. No.: 299,075

[22] Filed: Jan. 19, 1989

Related U.S. Application Data

[62] Division of Ser. No. 135,086, Dec. 18, 1987, Pat. No. 4,845,243.

[30] Foreign Application Priority Data

Dec. 23, 1986 [IT] Italy .................. 22825 A/86

[51] Int. Cl.$^5$ .................. C07C 63/36; C07C 63/04
[52] U.S. Cl. .................. 562/490; 562/493
[58] Field of Search .......... 549/296, 60, 499; 562/490, 493; 546/283

[56] References Cited

FOREIGN PATENT DOCUMENTS 0214426 3/1987 European Pat. Off. .

*Primary Examiner*—C. Warren Ivy
*Assistant Examiner*—A. Owens
*Attorney, Agent, or Firm*—Parkhurst, Wendel & Rossi

[57] ABSTRACT

Compounds of formula

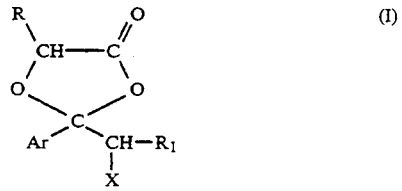

(wherein Ar, R, $R_1$ and X have the meaning reported in the description) are useful intermediates for the preparation of a variety of organic compounds, also optically active, like alpha-haloketones, alpha-hydroxyketones or ketals, alpha-arylalkanoic acids.

1 Claim, No Drawings

INTERMEDIATES AND THEIR USE IN THE SYNTHESIS OF ORGANIC COMPOUNDS

This is a division of application Ser. No. 07/135,086 filed Dec. 18, 1987 now U.S. Pat. No. 4,845,243.

The present invention concerns new intermediates for organic synthesis and more particularly it concerns new intermediates useful for the preparation of different organic compounds also of optically active organic compounds, such as alpha-haloketals, alpha-hydroxyketones or ketals (acetals) and alpha-arylalkanoic acids.

Object of the present invention are the compounds of formula:

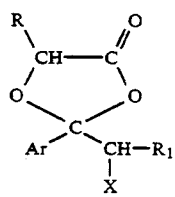
(I)

wherein
Ar represents an aryl or heteroaryl group having 5, 6 or 10 atoms in the aromatic structure and optionally substituted by from 1 to 3 substituents selected from the group consisting of $C_1-C_4$ alkyl, $C_1-C_4$ alkoxy, $C_1-C_4$ haloalkyl, $C_1-C_4$ haloalkoxy, phenyl or heteroaryl having 5 or 6 atoms, phenoxy, benzoyl, heteroaroyl and halogen atoms, each aromatic radical being optionally substituted by 1 or 2 substituents selected from the group consisting of halogen atoms, $C_1-C_4$ alkyl and $C_1-C_4$ alkoxy;
R represents a methyl or phenyl;
$R_1$ represents a $C_1-C_4$ alkyl;
X represents a chlorine, bromine or iodine atom.

The compounds of formula I are useful intermediates in organic synthesis as herebelow discussed.

In the meanings of Ar specific examples are phenyl, naphthyl, pyridyl, pyrrolyl, furyl, thienyl, thiazolyl, oxazolyl and isoxazolyl.

Specific examples of substituted aryl groups include 4-chlorophenyl, 4-isobutyl-phenyl, 4-difluoromethoxyphenyl, 3-phenoxyphenyl, 4-(2-thienylcarbonyl)-phenyl, 4-diphenyl, 6-methoxy-2-naphthyl, 5-chloro-6-methoxy-2-naphthyl, 5-bromo-6-methoxy-2-naphthyl, 6-hydroxy-2-naphthyl, 5-bromo-6-hydroxy-2-naphthyl.

Preferred meanings of $R_1$ are methyl and isopropyl.

The preparation of the compounds of formula I is carried out by halogenation of the compounds of formula

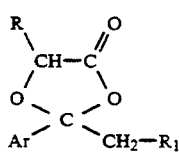
(II)

wherein Ar, R and $R_1$ have the meanings reported for formula (I). The halogenation is carried out by means of usual halogenating agents, in acidic conditions, in an inert solvent and at a temperature comprised between −50° C. and room temperature.

Preferred halogenating agents are ammonium or phosphonium perhalogenides, N-chloro, N-bromo or N-iodo-succinimide, cupric bromide, hexachloro-cyclohexadienone, alkyl or alkaline hypochlorite, iodine, iodine chloride and bromine.

The most preferred halogenating agent is bromine, which affords the compounds of formula I in which X=Br, due to its low cost. The compounds of formula II can easily be prepared according to known procedures described for example in J. Am. Chem. Soc., 99, 6038, (1977), Bull. Soc. Chim. Fr., 332, (1970), Zh. Org. Khim., 9, 1145, 51973), (C.A., 79:78654s).

A general procedure for the preparation of the compounds of formula II comprises the condensation of a ketone of formula

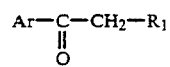
(III)

wherein Ar and $R_1$ have the above reported meanings, with a carboxylic acid or a reactive derivative thereof, of formula

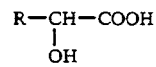
(IV)

wherein R has the above reported meanings.

The condensation is carried out in an inert solvent, that in some cases may be an excess of compound III, and in the presence of an acid, for example sulphuric or p.toluensulphonic acid.

The water formed during the reaction must be withdrawn from the reaction mixture for example by distillation or by chemical means. The condensation may be carried out on compounds III and IV as such or they may be used in masked form.

Examples of ketones of formula III in masked form are the compounds in which the carbonyl function is masked as dichloroderivative or acetal or enolether.

Instead of the acids of formula IV the analogs in which the alcoholic OH group is replaced by a halogen atom and their silylethers may be used.

When, instead of the ketones of formula III, the ketones already alpha-functionalyzed of formula

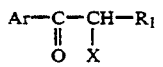
(III-A)

are used, the compounds of formula I are directly obtained.

The compounds of formula I can be used as intermediates in the synthesis of alpha-arylalkanoic acids.

In fact, they can be the rearranged providing, according to the operative conditions, the alpha-arylalkanoic acids of formula

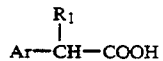
(V)

(wherein Ar and $R_1$ have the meanings reported for formula I) or their precursors like their esters. The hydrolysis of these affords the acids of formula V.

The experimental conditions in which the rearrangement reaction is carried out are similar to those known for the rearrangement of ketals, for example in the European patents 34871 and 35305 (Blaschim S.p.A.), 101124 and 151817 (Zambon S.p.A.).

The compounds of formula I, however, are characterized by a chemical reactivity which is due to the presence of a carbon atom carrying both an ether and ester function. They can be defined as lactones.

Compounds of formula I may be rearranged by treatment with a "soft" or "border line" Lewis acid (J. March, "Advanced Organic Chemistry" 3rd Ed., J. Wiley & Sons, page 229) or by treatment with a mixture of a polar aprotic solvent with a protic solvent having a high dielectric constant.

Alternatively, the compounds of formula I can be rearranged by treatment with water at acidic pH.

A preferred embodiment of the invention comprises the halogenation of the compounds of formula II in optically active form.

Said compound have two asimmetric carbon atom marked by an asterisk in the formula herebelow reported

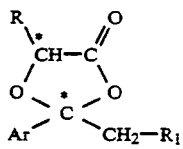
(II-A)

wherein Ar, R and $R_1$ have the above reported meanings.

The compounds of formula II-A are easily prepared, according to the same procedure above described for the preparation of the compounds of formula II, starting from the ketones of formula III, and the single enantiomers of the compounds of formula IV with reference to the carbon atom bonded to the R substituent.

Examples of optically active alpha-hydroxy acids useful for the preparation of the compounds of formula II-A are S(+)-lactic acid, R(−)-lactic acid, S(+)-mandelic acid and R(−)-mandelic acid.

The single enantiomers of lactic and mandelic acid by reaction with the ketones of formula III afford the compounds of formula II-A wherein R is methyl or phenyl respectively.

The compounds of formula II-A can be functionalized according to what above described, to obtain the compounds of formula

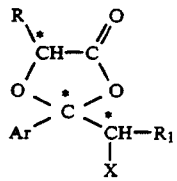
(I-A)

wherein Ar, R, $R_1$ and X have the above reported meanings and the asterisk indicate the asimmetric carbon atoms.

The rearrangement of compounds I-A according to the procedures above described affords the optically active alpha-arylalkanoic acids of formula

(V-A)

(wherein Ar and $R_1$ have the above reported meanings and the asterisk indicates the asimmetric carbon atom) or their precursors such as the corresponding esters.

It is worth noting that the rearrangement of the compounds of formula I-A affords the optically active alpha-arylalkanoic acids V-A having an enantiomeric excess consistent with the stereoisomeric excess of the starting compounds.

The compounds of formula I-A are also useful intermediates for the synthesis of other optically active compounds.

In fact, the hydrolysis of compounds I-A carried out in acid as well as in basic conditions affords optically active ketones of formula

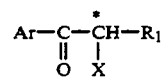
(VI)

wherein Ar, $R_1$ and X have the same meanings as those reported for formula I.

The reaction of the compounds of formula I-A with an alkaline alcoholate affords optically active alpha-hydroxyketals of formula

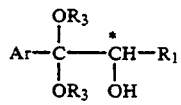
(VII)

wherein Ar and $R_1$ have the above reported meanings and $R_3$ is the residue of the used alkaline alcoholate. Thus, for example, when the alcoholate is sodium methoxide $R_3$ is methyl.

The optically active ketones and ketals of formulae VI and VII respectively are intermediates for the synthesis of alpha-arylalkanoic acids according to known procedures that comprise, in the case of the ketones VI, their transformation into optically active ketals and the rearrangement of these latters [European patent applications 81993 (Syntex Co.), 154853 and 153701 (Zambon S.p.A.)].

The most characterizing feature of the compounds of formula I-A is the possibility of preparing them diastereoselectively.

In fact the halogenation of the compounds of formula II-A (obtained by a single enantiomer of lactic or mandelic acid) is diastereoselective.

Let us assume that the configuration of the two carbon atoms marked by an asterisk in formula II-A is established (e.g. both have S configuration).

The halogenation of said compound affords the corresponding compound I-A as a mixture of two diastereoisomers (S,S,R and S,S,S) with reference to carbon atom bonded to the halogen atom X, in which one of the two diastereoisomers strongly prevail over the other.

We have also found that the configuration of the tertiary carbon atom of the ring is the one that predominantly influence the configuration of the new asimmetric carbon that is created by the halogenation.

Therefore the halogenation is diastereoselective and, accordingly, it is possible to have available the compounds of formula I-A enriched in one of the possible diastereoisomers. When desired, but generally it is not necessary, it is possible to further enrich the mixture in the desired diastereoisomer by conventional separation methods.

The diastereoselective halogenation is a particularly important feature because it allows to obtain the compounds of formula I-A from which various optically active intermediates and end-products may be obtained.

Among these it is worth citing S(+)-2-(6-methoxy-2-naphthyl)-propionic acid (V-A, Ar=6-methoxy-2-naphthyl, $R_1$=CH$_3$) an antiinflammatory drug know as Naproxen or its precursors like its esters and S(+)-2-(5-bromo-6-methoxy-2-naphthyl)-propionic acid and esters thereof.

Among the optically useful compound which can be prepared starting from the compounds of formula I-A may be cited the following acids which are intermediates in the synthesis of pyrethroid insecticides: S(+)-2-(4-chlorophenyl)-3-methyl-butirric acid (V-A, Ar=4-chlorophenyl, $R_1$=isopropyl) and S(+)-2-(4-difluoromethoxy-phenyl)-3-methyl-butirric acid (V-A, Ar=4-difluoromethoxyphenyl, $R_1$=isopropyl).

In order to better illustrate the invention the following examples are given.

EXAMPLE 1

Preparation of 2-(1-bromoethyl)-2-phenyl-5(S)-methyl-1,3-dioxolane-4-one

The compound 2-ethyl-2-phenyl-5(S)-methyl-1,3-dioxolane-4-one was prepared starting from propiophenone and S(+)-lactic acid according to the procedure described in J. Am. Chem. Soc., 99, 6038, (1977) or as described in Bull. Soc. Chim. Fr., 332, (1970).

To a solution of 2-ethyl-2-phenyl-5(S)-methyl-1,3-dioxolane-4-one (1 mmol) and hydrogen bromide (0.1 mmol) in carbon tetrachloride (3 ml), bromine (1 mmol) was added and the temperature was kept at 15° C.

After complete conversion, the reaction mixture was diluted with methylenechloride and washed with water. The organic phase was separated and dried on sodium sulphate. After evaporation of the solvents under vacuum 2-(1-bromoethyl)-2-phenyl-5(S)-methyl-1,3-dioxolane-4-one was obtained as a mixture of 4 diastereoisomers one of which strongly prevails.

EXAMPLE 2

Preparation of 2-phenyl-propanoic acid

Silver tetrafluoroborate (0.974 g; 5 mmol) was added at 15° C. to a solution of the diastereomeric mixture of 2-(1-bromoethyl)-2-phenyl-5-(S)-methyl-1,3-dioxolan-4-one (see example 1; 1.425 g; 5 mmol) in methanol (10 ml).

The reaction mixture was kept at 15° C. until complete conversion, diluted with water, and extracted with dichloromethane. The combined organic extracts were washed with water and dried over sodium sulfate. Evaporation of the solvent and purification of the crude by column chromatography gave the optically active 2-phenyl-propanoic acid methyl ester which by hydrolisis in acid conditions afforded the optically active free acid.

What we claim is:

1. A process for the preparation of optically active alpha-arylalkanoic acid of formula

wherein Ar represents an aryl group optionally substituted by 1 to 3 substituents selected from the group consisting of $C_1$–$C_4$ alkyl, $C_1$–$C_4$ alkoxy, $C_1$–$C_4$ haloalkyl, $C_1$–$C_4$ haloalkoxy, or phenyl, phenoxy, benzoyl, and halogen atoms, each aromatic radical being optionally substituted by 1 or 2 substituents selected from the group consisting of halogen atoms, $C_1$–$C_4$ alkyl and $C_1$–$C_4$ alkoxy; and $R_1$ represents a $C_1$–$C_4$ alkyl which process comprises rearrangement of an optically active compound of the formula:

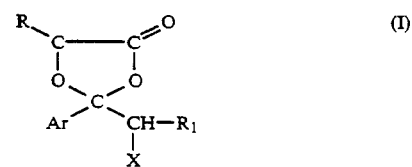

wherein R represents a methyl or phenyl group and X represents a chlorine, bromine or iodine atom;

said rearrangement being performed by treatment with (1) a soft or border line Lewis acid; (2) a mixture of a polar aprotic solvent with a protic solvent having a high dielectric constant; or (3) water at acidic pH.

* * * * *